(12) United States Patent
Videen

(10) Patent No.: US 6,958,812 B1
(45) Date of Patent: Oct. 25, 2005

(54) SYSTEMS AND METHODS FOR ANALYZING PARTICLE SYSTEMS OF SURFACE FACETS USING POLARIZED SCATTERED LIGHT

(75) Inventor: Gorden Videen, Silver Spring, MD (US)

(73) Assignee: The United States of America as represented by the Secretary of the Army, Washinton, DC (US)

( * ) Notice: Subject to any disclaimer, the term of this patent is extended or adjusted under 35 U.S.C. 154(b) by 213 days.

(21) Appl. No.: 10/642,677

(22) Filed: Aug. 19, 2003

(51) Int. Cl.[7] .......................... G01N 21/00; G01J 4/00
(52) U.S. Cl. ...................... 356/338; 356/364; 356/438
(58) Field of Search ............................... 356/337, 338, 356/340, 342, 364, 438, 439, 441, 442

(56) References Cited

U.S. PATENT DOCUMENTS

| | | | |
|---|---|---|---|
| 4,492,467 A * | 1/1985 | Drain et al. ................ | 356/336 |
| 4,770,529 A | 9/1988 | Levinson, et al. .......... | 356/153 |
| 5,028,119 A | 7/1991 | Hegg, et al. ................ | 350/174 |
| 5,060,063 A | 10/1991 | Freeman .................... | 358/101 |
| 6,052,187 A | 4/2000 | Krishnan, et al. ........... | 356/364 |
| 6,097,488 A | 8/2000 | Grek, et al. ................ | 356/364 |
| 6,124,928 A | 9/2000 | Slater ........................ | 356/317 |
| 6,138,083 A | 10/2000 | Videen ...................... | 702/155 |
| 6,163,408 A | 12/2000 | Larussa ..................... | 359/630 |
| 6,239,873 B1 | 5/2001 | Videen ...................... | 356/369 |
| 6,411,441 B1 | 6/2002 | Videen ...................... | 359/631 |
| 6,414,797 B1 | 7/2002 | Videen ...................... | 359/631 |

OTHER PUBLICATIONS

U.S. Appl. No. 09/707,291, entitled Wide-Angle Backscatter Probe Having a Rotatable Beamsplitter and Method of Measuring With Same, filed Nov. 6, 2000.

Yu. G. Shkuratov, M.A. Kreslavsky, A.A. Ovcharenko, D.G. Stankevich, and E.S. Zubko; Opposition Effect from Clementine Data and Mechanisms of Backscatter; 1999; pp. 132-155.

Vera K. Rosenbush, Viktor V. Avramchuk, and Aleksandr E. Rosenbush; Polarization Properties of the Galilean Satellites of Jupiter: Observations and Preliminary Analysis; Sep. 20, 1977; pp. 402-414.

Karri Muinonen; Coherent Backscattering by Solar System Dust Particles; 1993; pp 271-296.

Yu. Shkuratov, A. Ovcharenko, and E. Zubko, O. Miloslavskaya, K. Muinonen, J. Piironen, R. Nelson, W. Smythe, V. Rosenbush, and P. Helfenstein; The Opposition Effect and Negative Polarization of Structural Analogs for Planetary Regoliths; 2002; pp 396-416.

Michael I. Mishchenko; On the Nature of the Polarization Opposition Effect Exhibited by Saturn's Rings; The Astrophysical Journal; Jul. 1, 1993; pp 351-361.

M. I. Mishchenko; Polarization Effects in Weak Localization of Light: Calculation of the Copolarized and Depolarized Backscattering Enhancement Factors; Physical Review B; Dec. 1991; pp 597-600.

(Continued)

*Primary Examiner*—Gregory J. Toatley, Jr.
*Assistant Examiner*—Roy M. Punnoose
(74) *Attorney, Agent, or Firm*—William Randolph

(57) ABSTRACT

Methods for analyzing particle systems of surface facets using polarized scattered light are provided. An exemplary method comprises the steps of: providing models of multiple arbitrary particle systems, the particle system comprising surface facets; performing ray-trace analysis with respect to the models over a range of back-scatter angles, the ray-trace analysis involving only use of second-order rays; receiving information corresponding to a particle system of interest; and predicting at least one characteristic of the particle system of interest using information generated during the ray-trace analysis. Systems and other methods are provided.

20 Claims, 5 Drawing Sheets

SYSTEM OF SURFACE FACETS

OTHER PUBLICATIONS

M. I. Mishchenko; Enhanced Backscattering of Polarized Light from Discrete Random Media: Calculations in Exactly the Backscattering Direction; J. Opt. Soc. Am. A/vol. 9, No. 6/Jun. 1992; pp 978-982.

M. I. Mishchenko, Jean-Marc Luck, and Theo M. Nieuwenhuizen; Full Angular Profile of the Coherent Polarization Opposition Effect; J. Opt. Soc. Am. A/vol. 17, No. 5/May 2000; pp 888-891.

Ismo V. Lindell, Ari H. Sihvolva, Karri O. Muinonen, and Peter W. Barber; Scattering By a Small Object Close to an Interface; J. Opt. Soc. Am. A/vol. 8, No. 3/Mar. 1991; pp. 472-476.

K. O. Muinonen; A.H. Sihvola; I.V. Lindell; and K.A. Lumme; Scattering by a Small Object Close to An Interface; J. Opt. Soc. Am. A/vol. 8, No. 3/Mar. 1991; pp 477-482.

Karri Muinonen; Coherent Backscattering by Absorbing and Scattering Media; Sixth Conference on Light Scattering by Nonspherical Particles; pp 223-226.

J.E. Geak and M. Geake; A Remote-Sensing Method for Sub-Wavelength Grains on Planetary Surfaces by Optical Polarimetry; Mon. Nat. R. astr. Soc. (1990) 46-55.

Milo Wolff; Polarization of Light Reflected From Rough Planetary Surface; Applied Optics; Jun., 1975; pp 1395-1405.

K. Muinonen, M Kokko, S. Pohjolainen; and P. Hakala; Proceedings of the Finnish Astronomical Society; Observatory and Astrophysics Laboratory, University of Helsinki; 1990; pp 12-15.

Nadia T. Zakharova and Michael I. Mishchenko; Scattering Properties of Needlelike and Platelike Ice Spheriods With Moderate Size Parameters; Applied Optics/vol. 39, No. 27/ Sep. 20, 2000; pp 5052-5057.

* cited by examiner

SYSTEMS AND METHODS FOR ANALYZING PARTICLE SYSTEMS OF SURFACE FACETS USING POLARIZED SCATTERED LIGHT

GOVERNMENT INTEREST

The invention described herein may be manufactured, used, and licensed by or for the United States Government.

BACKGROUND

1. Technical Field

The disclosure relates to particle system analysis. More specifically, the disclosure relates to systems and methods that involve the use of polarization characteristics of light for analyzing particle systems that include surface facets.

2. Description of the Related Art

The polarization state of light is often described in relation to a plane of incidence defined by the vectors drawn in the direction of the incident and scattered rays. The transverse electric (TE) polarization refers to the polarization state of the light, the electric field vectors of which oscillate transverse, or perpendicular to this plane of incidence. The transverse magnetic (TM) polarization refers to the polarization state of the light, the magnetic field vectors of which oscillate transverse, or perpendicular to this plane of incidence. When a complex particle system having no preferentially oriented structure is illuminated by unpolarized light, the polarization state of the scattered light in the near-backward direction (i.e., within approximately 10 or 20 degrees of the exact backscatter direction) may be biased in favor of the TM state. Because fundamental physical processes like dipole scattering and Fresnel reflections favor the TE polarization state, this state is, perhaps, more commonly seen. A bias toward the TM-state is referred to as negative polarization and this negative polarization in the near backward-scatter (~<10 degrees from exact back-scatter) is sometimes referred to as the "Polarization Opposition Effect" (POE). Based on symmetry considurations, we expect the polarization in the exact backscatter direction to be zero.

There appears to be two branches to the negative polarization bias or POE. One branch manifests itself as an asymmetric dip in the linear polarization state at approximately or less than one degree from the exact backscatter direction. Another phenomena occurring in the near-backward-scattering direction is the photometric opposition effect. This refers to an increase in the absolute intensity of the scattered light in the backward direction. The maximum of this increase is located in the exact backward-scattering direction. Researchers observing astronomical bodies have observed that the minima position of the POE is located approximately at the half-width of the photometric opposition effect, i.e., the peak in the total intensity in the exact backscatter direction produced by the coherent backscattering mechanism, See, V. K. Rosenbush, V. V. Avramchuk, A. E. Rosenbush, and M. I. Mishchenko, "Polarization properties of the Galilean satellites of Jupiter: observations and preliminary analysis," Astrophys. J. 487, 402–414 (1997), which is incorporated by reference herein.

Another branch appears to be symmetric and parabolically shaped and is located at larger scattering angles, approximately but not limited to 5°–20° from the exact backward-scattering direction. It has been observed that one or both of these negative polarizations may be present in the same scattering system. In this disclosure, both branches of the negative polarization phenomena are referred to as the polarization opposition effect (POE). An accounting of the long, interwoven history of the POE will not be provided, as much of this has been provided elsewhere, for instance by Muinonen, K. Muinonen, "Coherent backscattering by solar system dust particles," in Asteroids, Comets and Meteors, ed. by A. Milani, M. Di Martino, and A. Cellino (Kluwer, Dordrecht, 1974) 271–296, and Yu. Shkuratov, A. Ovcharenko, E. Zubko, V. Kaydash, D. Stankevich, V. Omelchencko, O. Miloslavaskaya, K. Muinonen, J. Piironen, S. Kaasalainen, R. Nelson, W. Smythe, V. Rosenbush and P. Helfenstein, "The opposition effect and negative polarization of structural analogs of planetary regoliths," Icarus 159, 396–416 (2002), each of which is incorporated herein by reference.

The asymmetric branch of the POE has been inextricably linked with another phenomena, coherent backscattering enhancement. M. I. Mishechenko, "On the nature of the polarization opposition effect exhibited by Saturn's rings," Astrophys. J. 411, 351, 361, which is incorporated herein by reference. When a light ray traverses through a random medium to a detector, it is accompanied by another ray striking all the elements of the system in reverse order. When the detector is in the exact backscatter direction, these rays constructively interfere, because they have traversed the same pathlength but in reverse directions. When the detector is not in the exact backscatter direction, the pathlengths of these two reciprocal rays are no longer identical and we see the intensity drop off because the constructive interference condition is not optimized. The width of this peak is inversely proportional to the difference in pathlength between these two rays.

In a flourish of research along parallel lines, various researchers were able to show that the coherent backscatter mechanism was also responsible for the asymmetric branch of the POE. Earlier approaches considered rigorous methods applicable to specific scattering systems, like the use of the vector theory of coherent backscattering for a semi-infinite medium of Rayleigh particles, (See, V. D. Ozrin, "Exact solution for the coherent backscattering of polarized light from a random medium of Rayleigh scatterers," Waves Random Media 2, 141–164 (1992); M. I. Mishchenko, "Polarization effects in weak localization of light: Calculation of the copolarized and depolarized backscattering enhancement factors," Phys. Rev. B 44, 12, 579–12, 600 (1991); M. I. Mishchenko, "Enhanced backscattering of polarized light from discrete random media," J. Opt. Soc. Am. A 9, 978–982 (1992); and M. I. Mishchenko, J.-M. Luck, and T. M. Nieuwenhuizen, "Full angular profile of the coherent polarization opposition effect," J. Opt. Soc. Am. A 176, 888–891 (2000), each of which is incorporated by reference herein), or a scattering from small particles near a surface, (See, I. V. Lindell, A. H. Sihovla, K. O. Muinonen, and P. W. Barber, "Scattering by a small object close to an interface. I. Exact image theory formulation," J. Opt. Soc. Am. A 8, 472–476 (1991); and K. O. Muinonen, A. H. Sihvola, I. V. Lindell, and K. A. Lumme, "Scattering by a small object close to an interface. I. Study of backscattering," J. Opt. Soc. Am. A 8, 477–482 (1991), each of which is incorporated by reference herein).

More recent approaches applied Monte-Carlo-type ray-tracing computations for a generated particle system, keeping track of the phase of the scattered rays (K. Muinonen, "Coherent backscattering by absorbing and scattering media," in Light Scattering by Nonshperical Particles, B. Gustafson, L. Kolkolova, and G. Videen, eds. (U.S. Army Research Laboratory, Adelphi, Md., 2002) 223–226, which is incorporated herein reference herein) or involved an approximate expression for the scattering by a population of scatters. See, Yu. Shkuratov, M. Kreslavsky, A. Ovcharenko, D. Stankevich, E. Zubko, C. Pieters, and G. Arnold, "Opposition effect from Clementine data and mechanisms of backscatter," Icarus 141, 132–155 (1999), which is also incorporated by reference herein. Although the theory developed by Mishchenko is valid for arbitrary scatters, it applies only to the exact backscattering direction and to the incoherent background and thus does not describe explicitly the POE. Although these methods are significantly different in approach, there are significant similarities in their results. Part of the reason for this is that the polarization state of light scattered from a Rayleigh particle and from a surface facet are similar.

FIG. 1 shows the polarizing properties of a Rayleigh particle and surface facets as a function of scattering angle. The scattered light from the surface facet is predicted solely from the Fresnel reflection coefficients. Specifically, polarization properties of a Raleigh scatterer and of large facets, who scatter into the far field is calculated by a single Fresnel reflection, are shown. Zero degrees is the forward scatter, measured from the specular direction, and 180° is the back-scatter direction. Although the polarization properties of a Rayleigh sphere are independent of material, those calculated with Fresnel reflections are dependent on material properties of the crystal. The refractive indices used in the simulation of FIG. 1 are $m_{water}=1.33+10^{-5}i$ and $m_{aluminum}=0.5+5.0i$.

Because the two branches of the POE have significantly different shapes and one or both may be present in a scattering system, there is some debate as to the underlying physical mechanism of the symmetric, parabolically shaped branch. This was the subject of several discussions at a North Atlantic Treaty Organization Advance Research Workshop on the "Optics of Cosmic Dust" held din Bratislava, Slovakia, 16–19 Nov. 2001. Some researchers argued that the coherent backscatter mechanism can explain the observations of both asymmetric and symmetric branches of the POE, whereas others did not believe that the evidence as yet presented provides an adequate proof of the mechanism. It appears that the source of some of the confusion is that, in the calculations of M. I. Mishchenko, J.-M. Luck, and T. M. Nieuwenhuizen, the POEs for a population of Rayleigh scatterers have the same asymmetric shape regardless of the mean free path. In fact, the polarization is even plotted as a function of a dimensionless parameter $q=kl\gamma$, where l is the mean free path (or average distance a ray will travel before interacting with another surface facet), k is the spatial frequency defined in terms of wavelength $\lambda$ as $k=2\pi/\lambda$, and $\gamma$ is the scattering angle measured from the backscatter direction; hence the angular minimum can be found directly from this plot as $$q_{min} \approx \frac{1.68}{kl}.$$

Other methodologies that are able to produce a more symmetric, parabolic branch at larger scattering angles are either approximate techniques or ones in which the physical mechanisms are not as transparent. The presence of sometimes one and sometimes both branches measured from the same object has served to add to the confusion. Adding fuel to the fire is the experimental research of Geake and Geake. See J. E. Geake and M. Geake, "A remote-sensing method for sub-wavelength grains on planetary surfaces by optical polarimetry," Mon. Notes R. Astron. Soc. 245, 46–55 (1990), which is incorporated herein by reference. They discovered that the angular minimal positions measured from the backscatter of their samples increase with particle size parameter. This is the opposite of what would be predicted by a coherent backscatter mechanism. Much of the current understanding of the POE is contained in four chapters (astronomical observations, laboratory measurements, theory, and numerical techniques) of a book written by participants of the aforementioned workshop; specifically, G. Videen and M. Kocifaj, eds., Optics of Cosmic Dust (Kluwer Academic, Dordrecht, The Netherlands, 2002), which is incorporated by reference herein.

One would expect that attempts have been made to explain the POE using a ray-tracing model reflecting off randomly oriented facets, and indeed this is the case. Wolff did a similar analysis over a quarter of a century ago, M. Wolff, "Polarization of light reflected from rough planetary surface," Appl. Opt. 14, 1395–1405 (1975), which is incorporated by reference herein, and this is a starting point. Wolff derived the polarization state of light considering both single and double reflections off facets. He found that negative polarizations only occur for multiple reflections when the vector connecting the facets is oriented perpendicular to the plane of incidence. Essentially, the planes of incidence of each of the individual reflections is nearly perpendicular to the plane of incidence of the scattering system. The shadowing factor introduced in Wolff's work selectively enhances this particular component to produce the necessary negative polarization. It is important to remember that Wolff's paper precedes the rapid development of the understanding of coherent backscatter phenomena that occurred in the 1980s, and so this effect is not included in Wolff's work. As it happens, in the two-reflection analysis, Wolff considered the intensities of the rays reflecting off the facets, rather than the electric field amplitudes. He therefore did not have a mechanism to include coherent backscattering in his formulation.

Other facet models have employed the coherent backscattering mechanisms, but have treated specific scattering systems. Shkuratov considered two pairs of facets and derived approximate analytical formulae for the backscattering polarization, Yu. Shkuratov, "New mechanism of the negative polarization of light scattered by atmosphereless cosmic bodes," Astronmicheskii Vestnik 23, 176–180 (1989), which is incorporated by reference herein. Muinonen used a facet analysis to analyze the backscattering polarization from a pair of spheres, K. Muinonen, "Scattering of light by solar system dust: the coherent backscatter phenomenon," in 1990 Proc. of the Finnish Astron. Soc. 12, which is also incorporated herein by reference.

SUMMARY

Systems and methods for analyzing particle systems of surface facets using polarized scattered light are provided. An exemplary embodiment of a method comprises the steps of: providing models of multiple particle systems, the particle systems comprising surface facets; performing ray-trace analysis with respect to the models over a range of scatter angles, the ray-trace analysis involving only use of second-order rays; receiving information corresponding to a particle system of interest; and predicting at least one characteristic of the particle system of interest using information generated during the ray-trace analysis.

Another embodiment of a method comprises the steps of: calculating relationships between polarization states and back-scatter angles with respect to multiple arbitrary particle systems, at least some of the particle systems comprising surface facets; receiving information corresponding to a particle system of interest; correlating the information received with the relationships calculated to determine a best fit based, at least in part, on a minimum value of the polarization state of the particle system of interest; and using the best fit to estimate at least one characteristic of the particle system of interest.

Computer-readable media are provided that have computer programs stored thereon for performing computer-implemented method steps. In an exemplary embodiment of a computer-readable medium, the method steps comprise: receiving information corresponding to a model of a particle system that comprises surface facets; generating information corresponding to polarization state and back-scatter angle of the model at different mean-free-path parameters (l) using second-order ray-trace analysis; receiving information corresponding to a particle system of interest; and predicting at least one characteristic of the particle system of interest using the information generated.

In another exemplary embodiment of a computer-readable medium, the method steps comprise: calculating relationships between polarization states and back-scatter angles with respect to multiple arbitrary particle systems, at least some of the particle systems comprising surface facets; receiving information corresponding to a particle system of interest; correlating the information received with the relationships calculated to determine a best fit based, at least in part, on a minimum value of the polarization state of the particle system of interest; and using the best fit to estimate at least one characteristic of the particle system of interest.

An exemplary embodiment of a system for analyzing a particle system using polarized scattered light comprises: a model of multiple particle systems comprising surface facets, the model being configured to provide information corresponding to polarization state and back-scatter angle of the multiple particle systems at multiple separation parameters (l) using second-order ray-trace analysis; and a computer operative to access the model, the computer being further operative to: receive information corresponding to a particle system of interest; and predict at least one characteristic of the particle system of interest using the information provided by the model.

Other devices, systems, methods, features and/or advantages will be or may become apparent to one with skill in the art upon examination of the following drawings and detailed description. It is intended that all such additional devices, systems, methods, features and/or advantages be included within this description.

BRIEF DESCRIPTION OF THE DRAWINGS

Many aspects of the disclosure can be better understood with reference to the following drawings. Note, the components in the drawings are not necessarily to scale. Also, like reference numerals designate corresponding parts throughout the several views.

DETAILED DESCRIPTION

As will be described here, systems and methods are provided for performing ray-tracing analysis for particle systems that include surface facets. For example, embodiments of the systems and methods can be used for performing ray-tracing analysis of a cloud of random crystals, the facets of which are much larger than the wavelength of the incident radiation. Thus, the facets obey Fresnel's law of refraction. In some embodiments, we only consider the second-order-ray-tracing contribution, i.e. the rays which interact with or encounter two facets before reaching an observer, e.g., a detector. We also consider a modification of these results to keep track of the phases of rays contributing to coherent backscatter. For completion, we reiterate much of these results, changing however the particular orientations of the crystal facets to reflect a standard spherical polar coordinate system.

Figure 1:
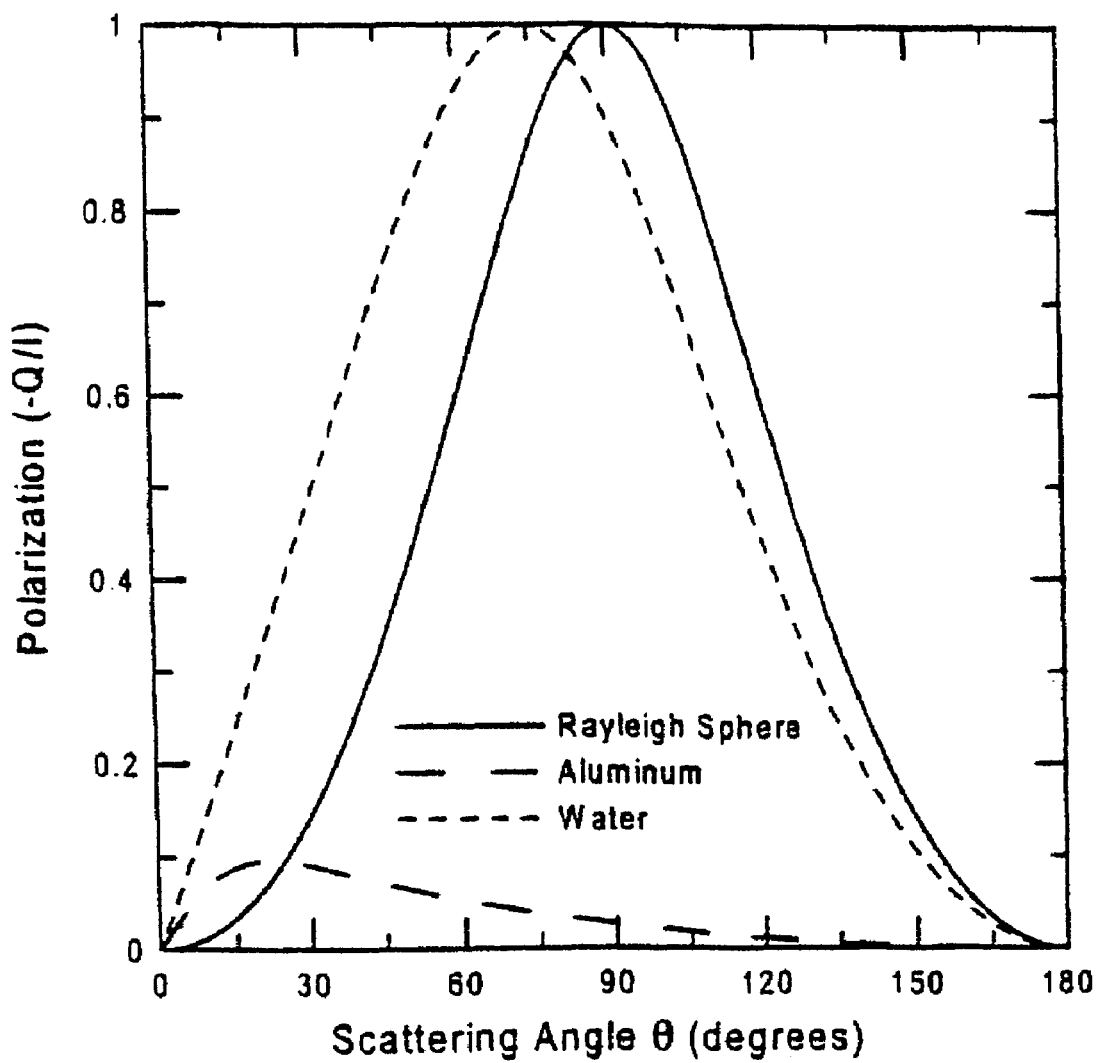
FIG. 1 is a graph depicting polarization versus scattering angle for a Rayleigh sphere and various surface facets.
Figure 2:
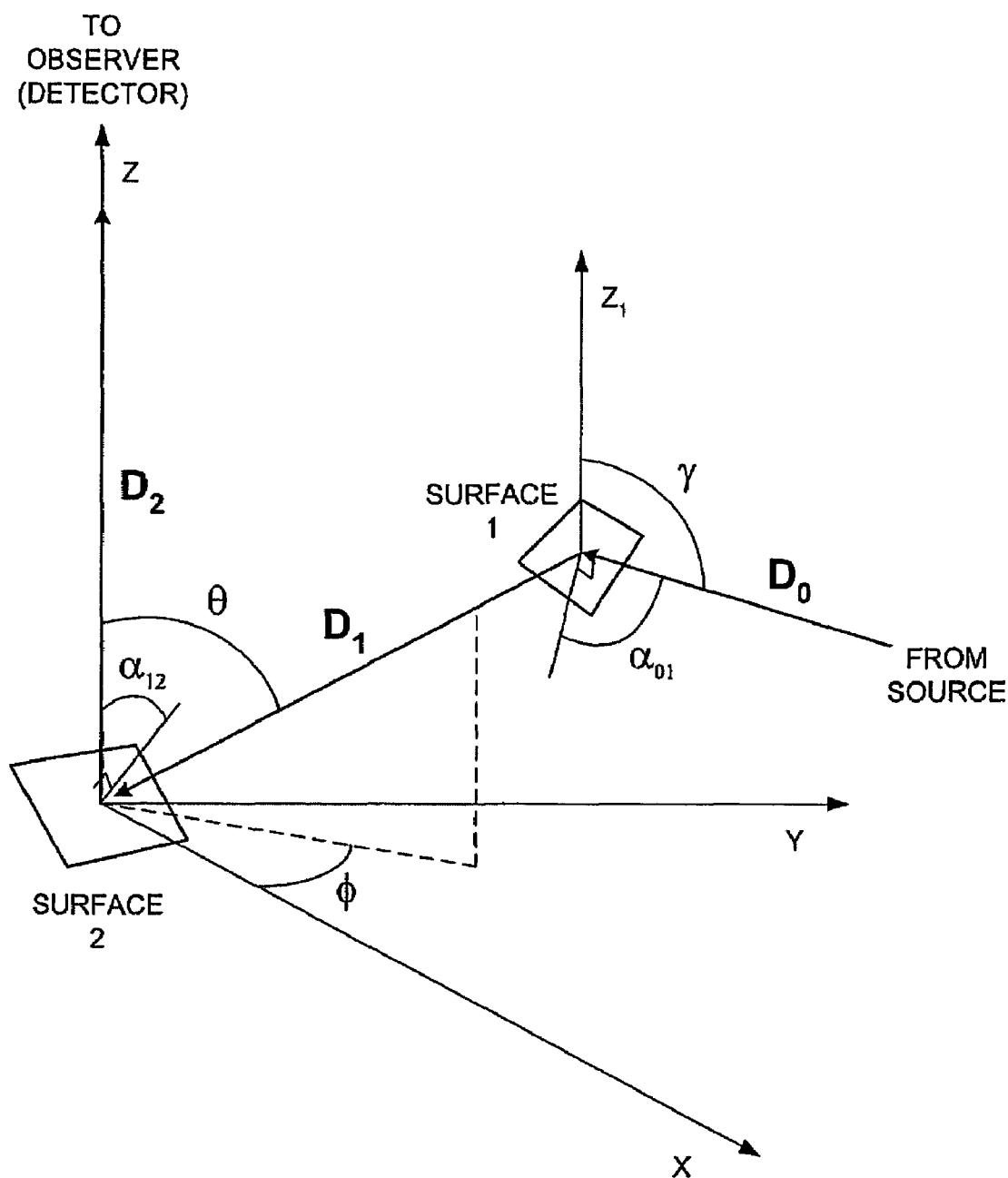
FIG. 2 is a schematic diagram depicting geometry of a representative particle system comprising surface facets.

A diagram of the scattering geometry is shown in FIG. 2. A light ray traveling in a plane parallel to the x-z plane, strikes Dipole 1 located at the point $(r, \theta, \phi)$. Backscatter angle $\gamma$ is defined as the angle between the incident field direction $D_0$ and the z axis. In the FIG. 2, the axis $z_1$ is parallel to the z axis. This ray travels in the direction of vector $D_0$. After reflecting off Facet 1, the ray, traveling in the direction of vector $D_1$, continues to Facet 2, which is located at the origin. The ray is then scattered in a direction parallel to the positive z axis, given by $D_2$, to the observer, e.g., a detector. The relevant unit ray vectors in Cartesian coordinates are given by $D_0 = (\sin \gamma, 0, -\cos \gamma)$ $D_1 = (-\sin \theta \cos \phi, -\sin \theta \sin \phi, -\cos \theta)$ $D_2 = (0,0,1).$     (2)

The incident angle at which the rays strike the facet are measured from the facet normals, as shown in FIG. 2, and are given by $$\alpha_{01} = \frac{1}{2}[\pi - \arccos(D_0 \cdot D_1)] \quad (3)$$

$$= \frac{1}{2}[\pi - \arccos(-\sin\theta\cos\phi\sin\gamma + \cos\theta\cos\gamma)],$$

$$\alpha_{12} = \theta/2.$$

The orientations of the planes of incidence are different for each facet. The orientation of the plane of incidence of Facet 1 with respect to Facet 2 is designated $\theta_{12}$ and is given by $$\cos\theta_{12} = \left(\frac{D_0 \times D_1}{|D_0 \times D_1|}\right) \cdot \left(\frac{D_1 \times D_2}{|D_1 \times D_2|}\right) \quad (4)$$

$$= \frac{\sin\theta\cos\gamma + \cos\theta\cos\phi\sin\gamma}{\sqrt{\sin^2\theta\sin^2\phi + (\sin\theta\cos\phi\cos\gamma + \cos\theta\sin\gamma)^2}}.$$

The last orientation of the scattering plane of incidence of Facet 2 to the system is designated $\theta_{20}$, and is given by $$\theta_{20} = \phi. \quad (5)$$

We consider the polarization states of the detected light separately. We assume that the light from the source is unpolarized. This light undergoes a Fresnel reflection from Facet 1 before striking Facet 2. To consider the effect of the second reflection we rotate the coordinate system, since the plane of incidence of the two facets is not the same. We again rotate the coordinate system to consider the light going to the observer. The electric fields of light scattered to the observer can be expressed as $$\begin{pmatrix} E_s \\ E_p \end{pmatrix} \sim \begin{pmatrix} \cos\phi & \sin\phi \\ -\sin\phi & \cos\phi \end{pmatrix} \begin{pmatrix} r_s(\alpha_{12}) & 0 \\ 0 & r_p(\alpha_{12}) \end{pmatrix} \times \quad (6)$$

$$\begin{pmatrix} \cos\theta_{12} & \sin\theta_{12} \\ -\sin\theta_{12} & \cos\theta_{12} \end{pmatrix} \begin{pmatrix} r_s(\alpha_{01}) & E_0 \\ r_p(\alpha_{01}) & E_0 \end{pmatrix},$$

where $E_0$ is the magnitude of the incident electric field on the system and $r_s$ and $r_p$ are the Fresnel reflection coefficients for s- and p-polarization states. S- and P-polarization states are also standard scientific notation: the s-polarization state is identical to the TE polarization state; the p-polarization state is identical to the TM polarization state. The "s" and "p" subscripts on the electric-field amplitudes and intensities refer to the components of these particular states. Note that, to this point, we have not included any of the phase information which would be necessary in a rigorous treatment of electric fields. We will proceed by expressing the intensities and incorporate the coherent backscattering factors in these expressions. Two things more need to be known about the scattering system to derive an expression for the observed intensities. First, it is necessary to know something about the scattering system, specifically the distribution of slopes of the facets $P_z$. Second, we need to know how far a ray can be expected to travel between facets 1 and 2 which we express as $P_x$. In this case, the total intensity is proportional to the sum of all the different orientations of the facets.

$$\begin{pmatrix} I_s \\ I_p \end{pmatrix} \sim \int \int \int \begin{pmatrix} E_s^* & E_s \\ E_p^* & E_p \end{pmatrix} P_{z'} P_X \cos\alpha_{12}\cos\alpha_{01}\sin\alpha_{12}dxd\alpha_{12}d\phi. \quad (7)$$

Note that $I_s = I_{TE}$ and is the intensity of the s-polarization state; $I_p = I_{TM}$ is the intensity of the p-polarization state.

At this point, we would like to make some assumptions about the scattering system so that we can obtain some results. First, we assume that the scattering system has no preferential orientation, i.e., the probability distribution of slopes is unity. The second quantity to be considered is the interaction distance $x = |D_1|$; i.e., the distance that the ray travels between facets 1 and 2. Although the rate of decay depends on the system being examined in our analysis:

$$I_2 = I_1 \exp(-\beta|D_1|), \quad (8)$$

i.e., the intensity at Facet 2, $I_2$, equals the intensity at Facet 1, $I_1$, multiplied by a decaying exponential, the argument of which is proportional to the distance between the two facets and inversely proportional to a characteristic length of the system $d = 1/\beta$. Note that the probability distributions chosen in this illustration are representative of the type of scattering system we are considering. For instance, this type of facet analysis is typical when considering a surface. However, the probability distributions on the mean free path are strongly dependent on the ray direction, and hence, the facet slope. The probability distributions we use are more characteristic of unaligned particles in a volume. This would correspond, for instance, to a cloud of facets having no preferential orientation. One advantage of the probability distributions we have chosen is that they allow one of the integrals to be solved analytically: Approximation (7) can be written as:

$$\begin{pmatrix} I_s \\ I_p \end{pmatrix} \sim \int \int \int \begin{pmatrix} E_s^* & E_s \\ E_p^* & E_p \end{pmatrix} \exp(-\beta x)\cos\alpha_{12}\cos\alpha_{01}\sin\alpha_{12}d\alpha_{12}dxd\phi. \quad (9)$$

We can include an interference mechanism that can include back-scattering enhancement by explicitly considering the interference between each set of reciprocal rays. The electric fields used in Approximation (9) now contain two reciprocal components:

$$E_s = E_s^{(1)} + E_s^{(2)}; \quad E_p = E_p^{(1)} + E_p^{(2)} \quad (10)$$

where $E_s^{(1)}$ is the complex amplitude of the ray from the source that strikes Facet 1, then Facet 2 before going to the observer (as shown in FIG. 2), and $E_s^{(2)}$ is the complex amplitude of the ray from the source that strikes Facet 2, then Facet 1 before going to the observer, and likewise for the p-component. We should make particular note that the second ray cannot, in general, be directed to the observer using strict geometrical optics, but will be directed to a point a certain angular extent from the z axis away from the observer. In fact, the second ray (coming from the source to Facet 2) in general will not even be reflected to Facet 1. From a strictly ray-tracing point of view, this is a serious problem. However, we must remember that, in general, we are considering observation positions very near the backward-scattering direction on the order of one degree. Although the facets are assumed to be large for a ray-tracing solution to be valid, they would have to be unrealistically large for the central lobe of the diffracted light to be less than a few degrees.

The electric field components now vary from each other by a phase difference $\exp(i\Phi)$ and the Eqn. 10 can now be written as $$E_s^* E_s = 2E_s^{(1)*} E_s^{(1)}(1 + \cos\Phi); \quad E_p^* E_p = 2E_p^{(1)*} E_p^{(1)}(1 + \cos\Phi), \quad (11)$$

where $$\Phi = k|D_1|(-\cos\theta + \sin\gamma\sin\theta\cos\phi + \cos\gamma\cos\theta) \quad (12)$$

$$= \alpha|D_1|.$$

Integrating Approximation (9) over the separation distance between the facets now yields $$\begin{pmatrix} I_s \\ I_p \end{pmatrix} \sim 2 \int \int \begin{pmatrix} E_s^{(1)*} & E_s^{(1)} \\ E_p^{(1)*} & E_p^{(1)} \end{pmatrix} \left( \frac{2\beta^2 + \alpha_2}{\beta^2 + \alpha_2} \right) \cos\alpha_{12} \cos\alpha_{01} \sin\alpha_{12} d\alpha_{12} d\phi. \quad (13)$$

Equation (10) provides second-order ray-tracing results of the s- and p-polarization intensities scattered by a cloud of facets. In many respects, it is an ideal system to study because all the physical mechanisms are transparent and elementary (i.e., Fresnel reflections and constructive interference), so we do not need to concern ourselves with other mechanisms clouding our interpretation of the results. Because of our particular choice of facet positions and orientations, the intensity solutions for a particular polarization state require only a single integration. Note also that this solution is not a Monte-Carlo type, but is in the form of an integral, so convergence is quite rapid.

Figure 3:
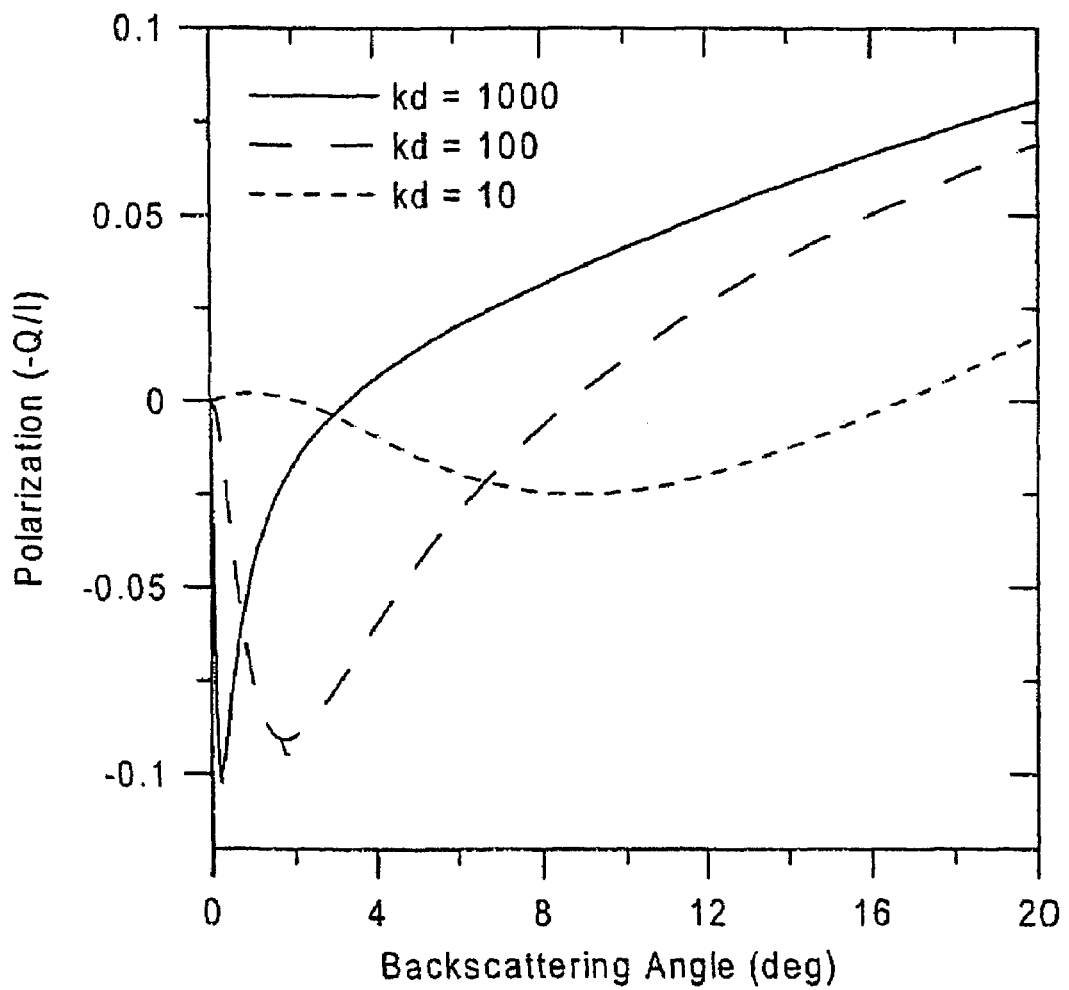
FIG. 3 is a graph depicting polarization versus back-scattering angle as calculated using second-order ray-tracing analysis for clouds of surface facets of three different spatial dimensions d.

FIG. 3 shows some sample calculations of the second-order ray-tracing results using Eqn. 10 for a cloud of facets (m=1.55+0.0i) for scattering systems having three different spatial dimensions d. For systems having relatively large spatial dimensions, kd=100, 1000, the POE is highly asymmetric with a minima located on the order of a degree. For systems having smaller spatial dimensions, kd=10, the POE takes on the characteristics of the parabolically shaped branch with a minima located in the tens of degrees. In our methodology, there are only two competing physical mechanisms; Fresnel reflections which serve to enhance the s-polarized light in a particular plane of incidence and constructive interference which enhances reciprocal rays whose phase difference is small. From Eqn. 12, smaller phase differences occur when Φ is near ±90. The two individual reflections from facet pairs in these orientations serve to enhance the p-polarization state of the scattered light. For systems having relatively small spatial dimensions, these phase differences have a negligible effect at small scattering angles. In this regime, geometrical factors serve to provide the s-polarized component with a greater enhancement. Although of interest from a physical standpoint, the magnitude of this positive region is extremely small and probably of little consequence in physical systems.

Thus, we have provided a second-order ray-tracing analysis of the polarization state of the scattered light from a cloud of facets with sizes much larger than the wavelength. To produce numerical results, we make two specific assumptions about the scattering system, that the probability distribution of facet slopes is uniform and that the probability function on the distance between interaction is a decaying exponential. Neither of these assumptions is consistent with a scattering surface. The scattering system resembles a cloud of randomly oriented facets. The results suggest that the two branches of the POE generated by such scattering systems are, in fact, a single branch. For separation parameters significantly larger than the wavelength, the POE is an asymmetric dip whose minima are located within a few degrees of the exact backscatter direction. When the spatial dimension d is on the order of the wavelength, the POE dip becomes more symmetric and parabolically shaped and the minimum may be located in the tens of degrees. The physical mechanism producing the dip is coherent scattering coupled with Fresnel reflections.

Figure 4:
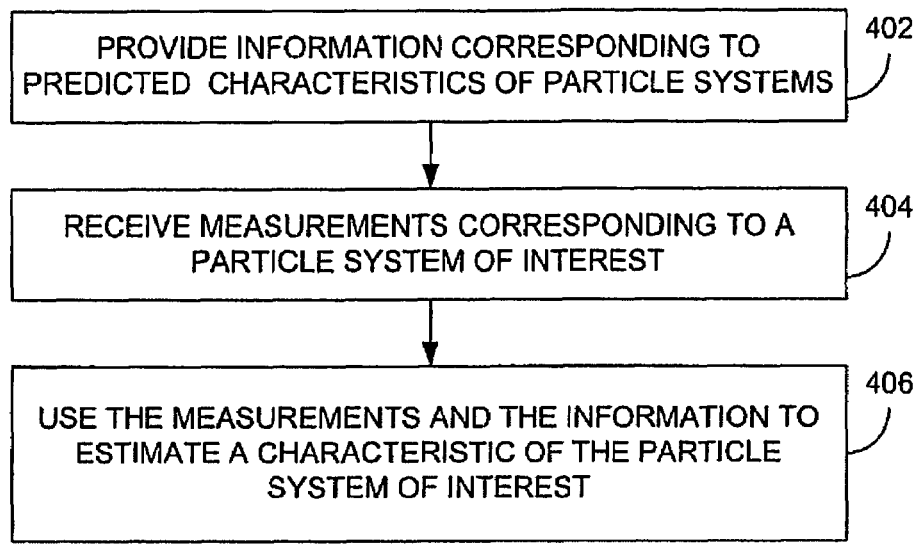
FIG. 4 is a flowchart depicting functionality of an embodiment of a system for analyzing particle systems of surface facets.

Having thus described the modeling theory, reference will now be made to FIGS. 4–7, which will be used to describe embodiments of systems and methods for analyzing particle systems of surface facets. As shown in FIG. 4, which is a flowchart depicting functionality of an embodiment of a system for analyzing particle systems of surface facets, the functionality (or method) may be construed as beginning at block 402, where information corresponding to predicted characteristics of particle systems is provided. By way of example, information can be obtained by performing ray-trace analysis on the model described above with respect to particle systems exhibiting a range of parameters. The information could be stored in graphical form or as entries in a database, for example, so that the information can be accessed when needed. In block 404, measurements corresponding to a particle system of interest are received. For instance, a detector placed in position with respect to a particle system of interest, such as depicted in FIG. 2, can be used to acquire measurements. Specifically, the measurements can include values of $I_{TM}$ and $I_{TE}$ over a range of back-scattering angles. These measurements can be used to calculate polarization percentages $(I_s-I_p/I_s+I_p)$ versus back-scattering angle. Then, in block 406, the measurements and the information are used to estimate a characteristic of the particle system of interest. In particular, the minimum values of the measured polarization of the particle system of interest can be correlated with the information obtained using the model.

Embodiments of systems for analyzing surface facets can be applied to the characterization of surfaces. This can include, for example, characterizing statistical properties of a rough surface, such as the separation between scattering sites, which would be related to the autocorrelation of the surface roughness. This might have applications in the production of surfaces used in nano-technology. Embodiments also could be used, for instance, in remote sensing applications (note that many of the references are remote-sensing work from astronomical bodies, Saturn's rings, the moon, Mars, asteroids and comets). Similarly, embodiment may be used for Earth remote sensing, which could be performed at longer wavelengths (microwave, radio waves, to look at larger scale features, etc.). Embodiments also may be used to characterize aerosol particles. Biological contaminants, like spores, might cluster, having a characteristic separation length, and a resulting prominent POE. Also possible is analyzing flaws in minerals (internal flaws, or facets), or underground surveying of the same on larger scales, using seismic waves (i.e., seismic s- and p-waves).

Systems for analyzing particle systems of surface facets can be implemented in software, firmware, hardware, or a combination thereof. When implemented in hardware, each of the systems can be implemented with any or a combination of various technologies. By way of example, the following technologies, which are each well known in the art, can be used: a discrete logic circuit(s) having logic gates for implementing logic functions upon data signals, an application specific integrated circuit (ASIC) having appropriate combinational logic gates, a programmable gate array(s) (PGA), and a field programmable gate array (FPGA).

When implemented in software, a system for analyzing particle systems typically is used in conjunction with a computer or processor-based device. An example computer that can be used to implement an embodiment of a system for analyzing particle systems is depicted in FIG. 5.

Figure 5:
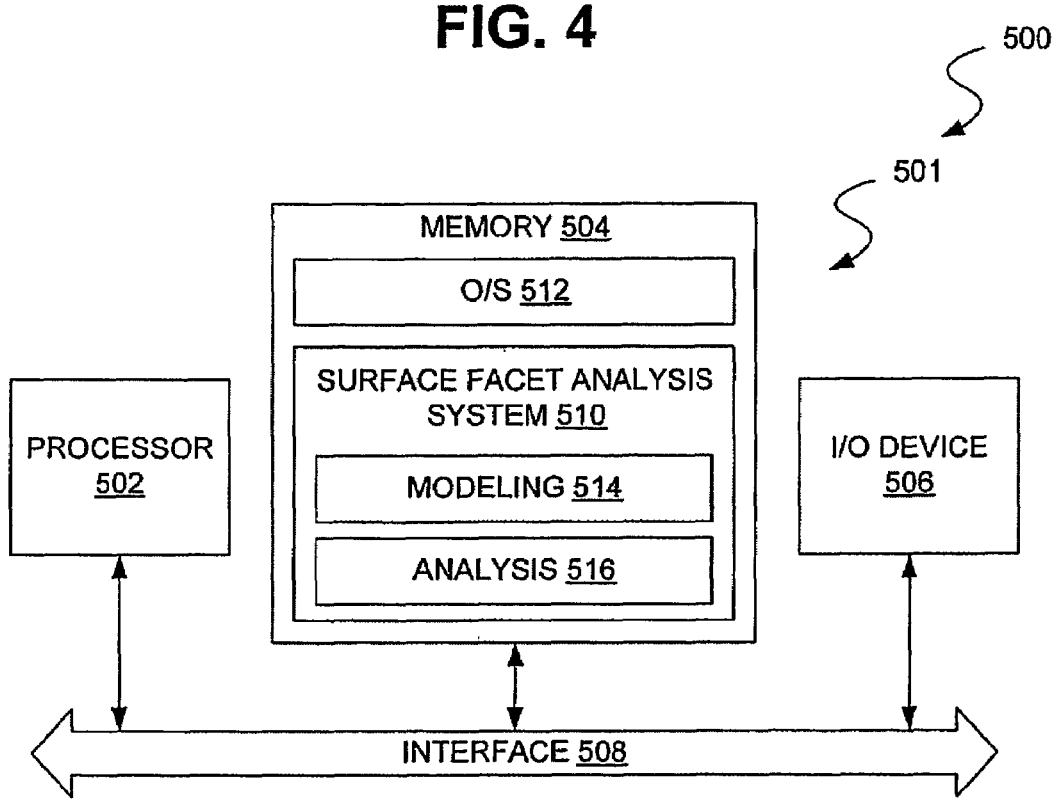
FIG. 5 is schematic diagram depicting a computer or processor-based system that can be used to implement an embodiment of a surface facet analysis system.

As shown in FIG. 5, an embodiment of a system for analyzing particle systems 500 includes a computer 501 that incorporates a processor 502, memory 504, and one or more input and/or output (I/O) devices 506 (or peripherals) that are communicatively coupled via a local interface 508. The software in memory 504 can include one or more separate programs, each of which comprises an ordered listing of executable instructions for implementing logical functions. In the example of FIG. 5, the software in the memory 504 includes a surface facet analysis system 510 and an operating system (O/S) 512. Note, surface facet analysis system 510 includes a modeling subsystem (module) 514 and an analysis subsystem (module) 516.

When surface facet analysis system 510 is implemented in software, it should be noted that the system can be stored on any computer-readable medium for use by or in connection with any computer-related system or method. In the context of this document, a computer-readable medium is an electronic, magnetic, optical, or other physical device or means that can contain or store a computer program for use by or in connection with a computer-related system or method. Surface facet analysis system 510 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

Functionality of the embodiment of the surface facet analysis system 510 of FIG. 5 will now be described with respect to the flowchart of FIG. 6. Note that the functions associated with the blocks of the flowchart of FIG. 6, or any of the other flowcharts of this disclosure, may occur out of the order in which they are depicted. In some embodiments, the functionality associated with multiple blocks could be executed substantially concurrently or sometimes in the reverse order.

Figure 6:
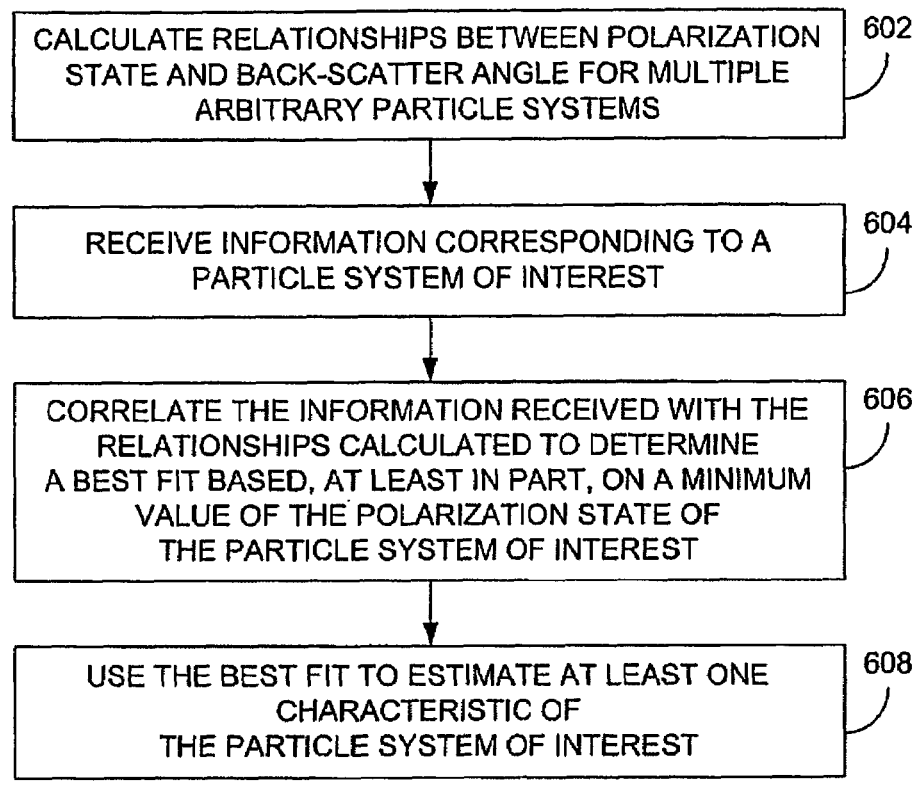
FIG. 6 is a flowchart depicting functionality of the embodiment of the surface facet analysis system of FIG. 5.

As shown in FIG. 6, the functionality (or method) may be construed as beginning at block 602, where relationships between polarization state and back-scatter angle are calculated for multiple arbitrary particle systems, at least some of which comprise surface facets. In block 604, information corresponding to a particle system of interest is received. In block 606, the information received is correlated with the relationships calculated to determine a best fit based, at least in part, on a minimum value of the polarization state of the particle system of interest. That is, the back-scattering angle at which the minimum polarization state occurs is compared to the back-scatter angles at which the minimum positions are predicted to occur for the arbitrary particle system to the model. In block 608, the best fit is used to estimate at least one characteristic of the particle system of interest. By way of example, in some embodiments, relationships between polarization state and back-scatter angle are calculated by a modeling subsystem, e.g., modeling subsystem 514, that implements the modeling theory described before. The functionality of such an embodiment will now be described with respect to the flowchart of FIG. 7.

Figure 7:
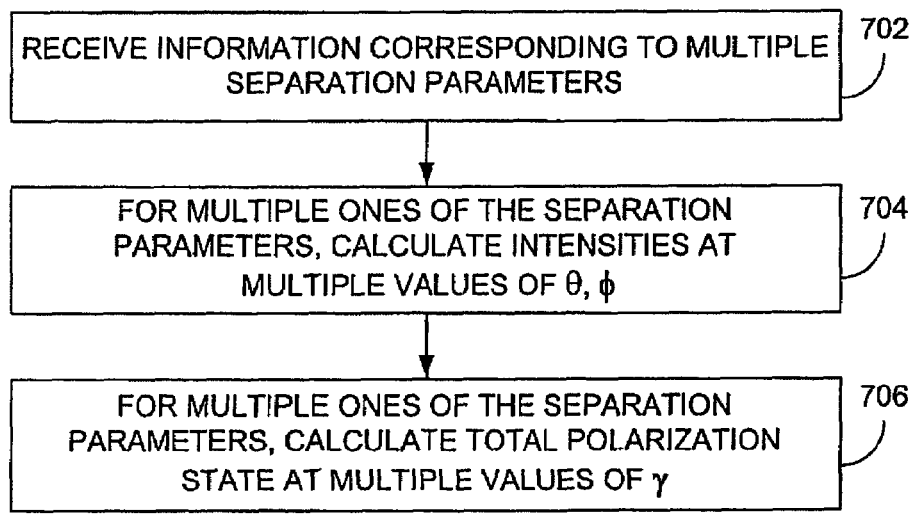
FIG. 7 is a flowchart depicting functionality of the embodiment of the analysis module of FIG. 5.

As shown in FIG. 7, the functionality (or method) of an embodiment of a modeling subsystem may be construed as beginning at block 702, where information corresponding to multiple separation parameters are received. In block 704, polarization intensities at multiple values of θ, φ are calculated for multiple ones of the separation parameters. In block 706, total polarization state at multiple values of γ are calculated for multiple ones of the separation parameters. Once calculated, the values can be stored in a memory storage device, e.g., memory 504, and accessed as needed.

It should be emphasized that many variations and modifications may be made to the above-described embodiments. All such modifications and variations are intended to be included herein within the scope of this disclosure and protected by the following claims.

What is claimed is:

1. A method for analyzing particle systems of surface facets using polarized scattered light, said method comprising the steps of:
providing models of multiple particle systems, the particle systems comprising surface facets;
performing ray-trace analysis with respect to the models over a range of scatter angles, the ray-trace analysis involving only use of second-order rays;
receiving information corresponding to a particle system of interest; and
predicting at least one characteristic of the particle system of interest using information generated during the ray-trace analysis.

2. The method of claim 1, wherein, in performing ray-trace analysis, Fresnel reflections are used.

3. The method of claim 1, wherein, in performing ray-trace analysis, constructive interference of the second-order rays is considered.

4. The method of claim 1, wherein, in performing ray-trace analysis, information corresponding to polarization state at near-back-scatter angles is generated for each of the models.

5. The method of claim 1, wherein providing models of multiple particle systems comprises the step of:
providing a model for each of multiple values of a separation parameter (l) for a selected particle size.

6. The method of claim 1, wherein predicting at least one characteristic of the particle system of interest comprises the step of:
comparing the information corresponding to the particle system of interest to the information generated to determine which model most closely corresponds to the particle system of interest.

7. The method of claim 1, wherein, in comparing the information corresponding to the particle system of interest to the information generated, the minimum values of polarization state versus back-scatter angles are compared.

8. The method of claim 1, wherein:
the method additionally comprises the step of:
detecting values of the intensities $I_{TM}$ and $I_{TE}$ at various back-scatter angles with respect to the particle system of interest; and
the information received corresponds to the values of $I_{TM}$ and $I_{TE}$ detected.

9. A method for analyzing particle systems of surface facets using polarized scattered light, said method comprising the steps of:
- calculating relationships between polarization states and back-scatter angles with respect to multiple arbitrary particle systems, at least some of the particle systems comprising surface facets;
- receiving information corresponding to a particle system of interest;
- correlating the information received with the relationships calculated to determine a best fit based, at least in part, on a minimum value of the polarization state of the particle system of interest; and
- using the best fit to estimate at least one characteristic of the particle system of interest.

10. The method of claim 9, wherein, in calculating relationships, Fresnel reflections are used.

11. The method of claim 10, in calculation relationships, second-order ray-trace analysis is performed with respect to at least some of the particle systems that comprise surface facets.

12. A computer-readable medium having a computer program stored thereon, the computer program being executable to perform computer-implemented method steps, said method steps comprising:
- receiving information corresponding to a model of a particle system that comprises surface facets;
- generating information corresponding to polarization state and back-scatter angle of the model at multiple separation parameters (l) using second-order ray-trace analysis;
- receiving information corresponding to a particle system of interest; and
- predicting at least one characteristic of the particle system of interest using the information generated.

13. The computer-readable medium of claim 12, wherein the method step of generating information comprises the step of using constructive interference of second-order rays.

14. The computer-readable medium of claim 12, wherein the method step of predicting at least one characteristic of the particle system of interest comprises the steps of:
- comparing the information corresponding to the particle system of interest to the information generated; and
- determining which separation parameter most closely corresponds to the particle system of interest based on the comparing step.

15. The computer-readable medium of claim 14, wherein the method step of comparing the information corresponding to the particle system of interest to the information accessed, the minimum values of polarization state versus back-scatter angles are compared.

16. A computer-readable medium having a computer program stored thereon, the computer program being executable to perform computer-implemented method steps, said method steps comprising:
- calculating relationships between polarization states and back-scatter angles with respect to multiple arbitrary particle systems, at least some of the particle systems comprising surface facets;
- receiving information corresponding to a particle system of interest;
- correlating the information received with the relationships calculated to determine a best fit based, at least in part, on a minimum value of the polarization state of the particle system of interest; and
- using the best fit to estimate at least one characteristic of the particle system of interest.

17. The computer-readable medium of claim 16, wherein, in calculating relationships, Fresnel reflections are used.

18. The computer-readable medium of claim 16, wherein, in calculating relationships, second-order ray-trace analysis is performed with respect to at least some of the particle systems that comprise surface facets.

19. A system for analyzing a particle system using polarized scattered light comprises:
- a model of multiple particle systems comprising surface facets, the model being configured to provide information corresponding to polarization state and back-scatter angle of the multiple particle systems at multiple separation parameters (l) using second-order ray-trace analysis; and
- a computer operative to access the model, the computer being further operative to:
  - receive information corresponding to a particle system of interest; and
  - predict at least one characteristic of the particle system of interest using the information provided by the model.

20. The system of claim 19, further comprising:
- means for storing the model such that the model is accessible by the computer.

\* \* \* \* \*